United States Patent
Hanebuchi et al.

(10) Patent No.: US 10,010,451 B2
(45) Date of Patent: Jul. 3, 2018

(54) OPHTHALMIC LASER SURGICAL APPARATUS

(71) Applicant: NIDEK CO., LTD., Gamagori, Aichi (JP)

(72) Inventors: Masaaki Hanebuchi, Aichi (JP); Naho Murakami, Toyokawa (JP); Takayoshi Shibata, Gamagori (JP); Shinya Iwata, Aichi (JP)

(73) Assignee: NIDEK CO., LTD., Aichi (JP)

( * ) Notice: Subject to any disclaimer, the term of this patent is extended or adjusted under 35 U.S.C. 154(b) by 769 days.

(21) Appl. No.: 14/460,778

(22) Filed: Aug. 15, 2014

(65) Prior Publication Data

US 2015/0051591 A1 Feb. 19, 2015

(30) Foreign Application Priority Data

Aug. 17, 2013 (JP) .................................. 2013-169308
Aug. 17, 2013 (JP) .................................. 2013-169309

(51) Int. Cl.
*A61F 9/008* (2006.01)

(52) U.S. Cl.
CPC .......... *A61F 9/008* (2013.01); *A61F 9/00825* (2013.01); *A61F 2009/0087* (2013.01);
(Continued)

(58) Field of Classification Search
CPC ............ A61F 2009/00897; A61F 9/008; A61F 9/00825; A61F 2009/00851; A61F 2009/0087; A61F 2009/00872
See application file for complete search history.

(56) References Cited

U.S. PATENT DOCUMENTS

2005/0228366 A1* 10/2005 Kessler ................. A61F 9/0084
606/5
2006/0195076 A1 8/2006 Blumenkranz et al.
(Continued)

FOREIGN PATENT DOCUMENTS

EP 2574318 A1 4/2013
JP 60-171043 A 9/1985
(Continued)

OTHER PUBLICATIONS

Search Report dated Jan. 23, 2015, issued by the European Patent Office in counterpart European Application No. 14180950.9.
(Continued)

*Primary Examiner* — Scott T Luan
(74) *Attorney, Agent, or Firm* — Sughrue Mion, PLLC

(57) ABSTRACT

An ophthalmic laser surgical apparatus includes an XY scan unit, a light guiding optical element, an objective lens, and a Z scan unit. The XY scan unit includes a deflecting device for deflecting the pulsed laser beam, and scans the pulsed laser beam in a direction crossing an optical axis. The light guiding optical element is provided downstream of the deflecting device on the optical path of the pulsed laser beam. The light guiding optical element has refractive power, and guides the pulsed laser beam. The objective lens causes the pulsed laser beam through the XY scan unit and the light guiding optical element to converge in a tissue of a patient's eye. The Z scan unit varies the optical path length between the light guiding optical element and the objective lens while the objective lens is fixed in position on the optical path.

11 Claims, 5 Drawing Sheets

(52) U.S. Cl.
CPC ............... *A61F 2009/00851* (2013.01); *A61F 2009/00872* (2013.01); *A61F 2009/00897* (2013.01)

(56) References Cited

U.S. PATENT DOCUMENTS

| | | |
|---|---|---|
| 2007/0291277 A1 | 12/2007 | Everett et al. |
| 2010/0191226 A1 | 7/2010 | Blumenkranz et al. |
| 2011/0028948 A1* | 2/2011 | Raksi ................. A61F 9/008 606/4 |
| 2011/0028951 A1 | 2/2011 | Raksi et al. |
| 2011/0178511 A1 | 7/2011 | Blumenkranz et al. |
| 2011/0178512 A1 | 7/2011 | Blumenkranz et al. |
| 2012/0310224 A1 | 12/2012 | Miyagi |
| 2012/0316545 A1 | 12/2012 | Blumenkranz et al. |
| 2013/0023864 A1 | 1/2013 | Blumenkranz et al. |
| 2013/0197634 A1 | 8/2013 | Palanker et al. |
| 2013/0338648 A1 | 12/2013 | Hanebuchi et al. |
| 2014/0228826 A1 | 8/2014 | Blumenkranz et al. |
| 2014/0228827 A1 | 8/2014 | Blumenkranz et al. |
| 2014/0316386 A1 | 10/2014 | Blumenkranz et al. |
| 2015/0038951 A1 | 2/2015 | Blumenkranz et al. |
| 2015/0038952 A1 | 2/2015 | Blumenkranz et al. |
| 2015/0141968 A1 | 5/2015 | Blumenkranz et al. |
| 2015/0366712 A1 | 12/2015 | Palanker et al. |
| 2016/0074214 A1 | 3/2016 | Palanker et al. |
| 2016/0074218 A1 | 3/2016 | Palanker et al. |
| 2016/0074229 A1 | 3/2016 | Palanker et al. |
| 2016/0213512 A1 | 7/2016 | Palanker et al. |
| 2016/0346119 A1 | 12/2016 | Palanker et al. |
| 2016/0354242 A1 | 12/2016 | Palanker et al. |
| 2016/0354247 A1 | 12/2016 | Palanker et al. |
| 2017/0027747 A1 | 2/2017 | Palanker et al. |

FOREIGN PATENT DOCUMENTS

| | | |
|---|---|---|
| JP | 2008-526384 A | 7/2008 |
| JP | 2012-249701 A | 12/2012 |
| JP | 2013-78398 A | 5/2013 |
| JP | 2013-78399 A | 5/2013 |
| WO | 2006074469 A2 | 7/2006 |
| WO | 2012178054 A1 | 12/2012 |

OTHER PUBLICATIONS

Communication dated Jun. 22, 2015 by the European Patent Office in related Application No. 14180950.9.

Communication dated May 2, 2017, issued by the Japanese Patent Office in counterpart Japanese Patent Application No. 2013-169309.

* cited by examiner

OPHTHALMIC LASER SURGICAL APPARATUS

CROSS REFERENCE TO RELATED APPLICATIONS

This application is based upon and claims the benefit of priorities of Japanese Patent Application No. 2013-169308 filed on Aug. 17, 2013 and Japanese Patent Application No. 2013-169309 filed on Aug. 17, 2013, the contents of which are incorporated herein by reference in its entirety.

BACKGROUND

The present disclosure relates to an ophthalmic laser surgical apparatus that converges a pulsed laser beam to a tissue of a patient's eye for the treatment of the patient's eye.

Various techniques are proposed that converge a pulsed laser beam to a three-dimensional target position in a patient's eye. For example, JP-A-2013-78399 discloses an ophthalmic laser surgical apparatus that includes an XY scan unit and an expander. The XY scan unit scans a laser beam's convergence position (laser spot) on an XY plane orthogonal to the optical axis. The expander is provided upstream of the XY scan unit, and moves a laser beam's convergence position along Z direction.

SUMMARY

For accuracy of treatment, it is desired that an ophthalmic laser surgical apparatus three-dimensionally scans the convergence position of a pulsed laser beam with high accuracy. However, an ophthalmic laser surgical apparatus needs to overcome a number of restrictions if the scanning of a convergence position were to be improved with a simple configuration. It has been difficult with conventional ophthalmic laser surgical apparatuses to properly scan the convergence position of a pulsed laser beam with a simple configuration.

The present disclosure is intended to typically provide an ophthalmic laser surgical apparatus that can properly scan the convergence position of a pulsed laser beam with a simple configuration.

One of aspects of the disclosure provides the following arrangements:

An ophthalmic laser surgical apparatus for converging a pulsed laser beam in a tissue of a patient's eye for the treatment of the eye, the apparatus comprising:

a laser light source configured to emit the pulse laser;

an XY scan unit which includes at least one deflecting device configured to deflect the pulsed laser beam emitted by the laser light source, and which is configured to scan the pulsed laser beam in a direction crossing an optical axis of the pulsed laser beam by the deflecting device;

a light guiding optical element provided downstream of the deflecting device of the XY scan unit on the optical path of the pulsed laser beam, the light guiding optical element having refractive power and guiding the pulsed laser beam toward the downstream side of the optical path;

an objective lens that causes the pulsed laser beam, which passes through the XY scan unit and the light guiding optical element, to converge in the tissue; and a Z scan unit configured to scan a convergence position of the pulsed laser beam in a Z direction along the optical axis by varying the optical path length between the light guiding optical element and the objective lens while the objective lens is fixed in position on the optical path.

An ophthalmic laser surgical apparatus for converging a pulsed laser beam in a tissue of a patient's eye for the treatment of the eye, the apparatus comprising:

an XY scan unit configured to scan the pulsed laser beam from a laser light source in a direction crossing an optical axis of the pulsed laser beam;

an objective lens disposed downstream of the XY scan unit on the optical path of the pulsed laser beam, the objective lens being configured to converge the pulsed laser beam passing from the XY scan unit; and a Z scan unit configured to scan a convergence position of the pulsed laser beam in a Z direction along the optical axis by moving at least a part of the XY scan unit along the optical axis.

The ophthalmic laser surgical apparatus according to the present disclosure can properly scan the convergence position of a pulsed laser beam with a simple configuration.

DESCRIPTION OF ILLUSTRATIVE EMBODIMENTS

First Embodiment

Figure 1:
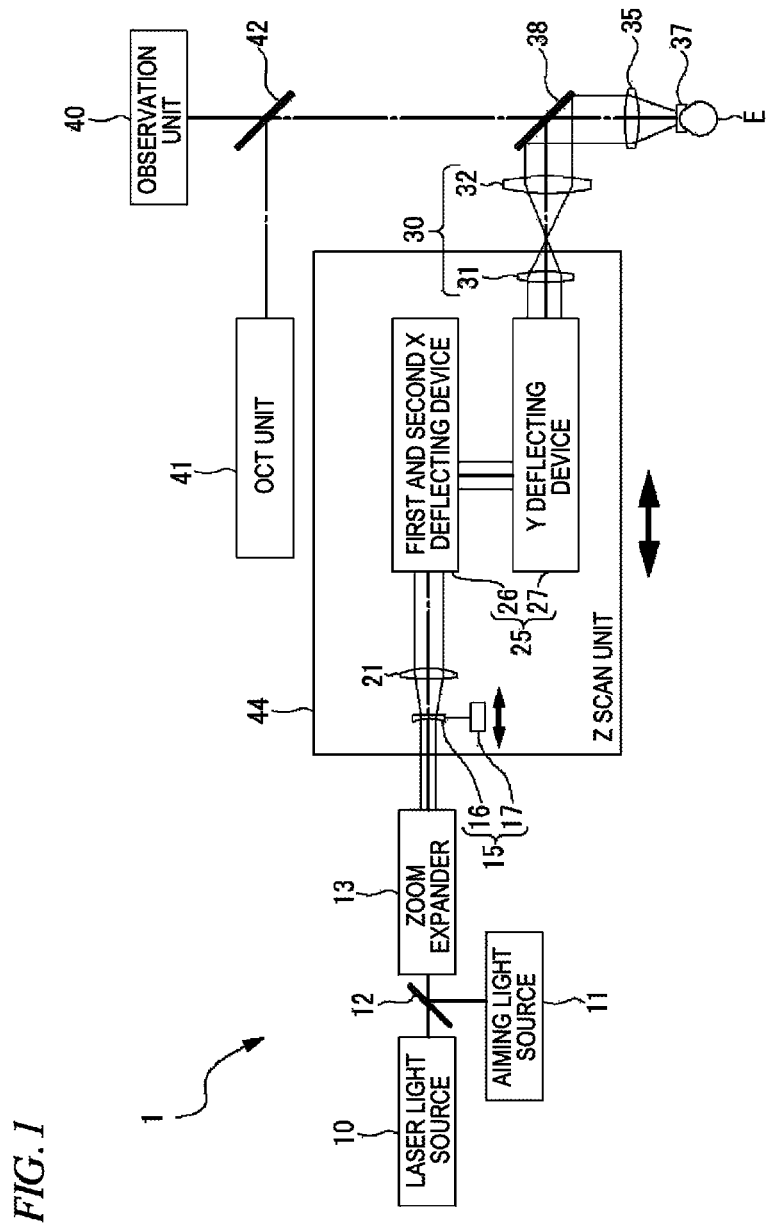
FIG. 1 is a diagram representing the configuration of the ophthalmic laser surgical apparatus of First Embodiment.

First Embodiment as an illustrative embodiment according to the present disclosure is described below with reference to FIGS. 1 to 3. The present embodiment is, for example, an ophthalmic laser surgical apparatus 1 that can treat both the cornea and the crystalline lens of patient's eye E. As used herein, "treat" means treating patient's eye E by means of, for example, cutting and disrupting an ocular tissue. The constituting elements of the ophthalmic laser surgical apparatus 1 of First Embodiment are described below, in order from a laser light source 10 (the upstream side of the pulsed laser beam optical path) to the patient's eye E (the downstream side of the pulsed laser beam optical path).

The laser light source 10 emits a pulsed laser beam. In the present embodiment, the pulsed laser beam emitted by the laser light source 10 converges in a tissue of patient's eye E, and generates a plasma that cuts and disrupts the tissue at the convergence position. This phenomenon is also known as photodisruption. The laser light source 10 may be realized by, for example, a device that emits a pulsed laser beam of a femtosecond- to picosecond-order pulse width. In the following, the direction along the optical axis of the pulsed laser beam emitted by the laser light source 10 will be referred to as Z direction. X direction is a direction that crosses the Z direction (perpendicularly in this embodiment). The direction that crosses the Z direction and the X direction (perpendicularly in this embodiment) is Y direction. X, Y, and Z directions may be appropriately set. For example, when specifying directions relative to a patient, X and Y directions may be horizontal and vertical directions, respectively, relative to the patient, and vice versa.

An aiming light source 11 emits an aiming beam that marks the position to be irradiated by the pulsed laser beam. In the present embodiment, the aiming light source 11 is realized by a light source that emits a visible laser beam. The aiming light source 11 may be omitted.

A dichroic mirror 12 is provided between the laser light source 10 and a zoom expander 13 (described later) on the pulsed laser beam optical path (hereinafter, also referred to simply as "optical path"). The dichroic mirror 12 combines the laser beam emitted by the laser light source 10, and the aiming beam emitted by the aiming light source 11. Specifically, the dichroic mirror 12 of the present embodiment combines these light beams by passing most of the laser beam emitted by the laser light source 10, and reflecting most of the aiming beam emitted by the aiming light source 11.

The zoom expander 13 is provided between the laser light source 10 and an XY scan unit 25 (described later) on the optical path. Specifically, in the present embodiment, the zoom expander 13 is provided between the laser light source 10 and a high-speed Z scan unit 15 (described later). The zoom expander 13 can vary the beam diameter (beam size) of the pulsed laser beam emitted by the laser light source 10. In one embodiment, the control unit (not illustrated) of the ophthalmic laser surgical apparatus 1 drives the zoom expander 13, and varies the beam diameter of the pulsed laser beam to adjust the numerical aperture NA of the pulsed laser beam that reaches patient's eye E through an objective lens 35 (described later). The numerical aperture NA increases as the beam diameter increases, and decreases as the beam diameter decreases.

By adjusting the numerical aperture NA, the ophthalmic laser surgical apparatus 1 can have improved capability for the treatment of patient's eye E. For example, the spot size at the convergence position of the pulsed laser beam becomes smaller as the numerical aperture NA increases. Corneal surgery often requires high accuracy for the convergence position of the pulsed laser beam for the precision of treatment. Crystalline lens surgery, on the other hand, may require a larger spot size for a shorter operation time. The ophthalmic laser surgical apparatus 1 of the present embodiment may thus operate to increase the numerical aperture NA and produce a smaller spot size in a corneal surgery mode than in a crystalline lens surgery mode. The numerical aperture NA may be decreased to produce a larger spot size in a crystalline lens surgery mode. In this way, the ophthalmic laser surgical apparatus 1 can provide a more appropriate treatment as may be decided according to the location of patient's eye E. The numerical aperture NA may be adjusted by appropriately using different methods. For example, the ophthalmic laser surgical apparatus 1 may vary the numerical aperture NA either continuously or intermittently according to the Z scan of a convergence position. In this case, the ophthalmic laser surgical apparatus 1 can appropriately photodisrupt the tissue according to the depth of the convergence position in Z direction.

The high-speed Z scan unit 15 (second Z scan unit: an expander in the present embodiment) is provided between the laser light source 10 and the XY scan unit 25 on the optical path (specifically, between the zoom expander 13 and the XY scan unit 25 in First Embodiment). The high-speed Z scan unit 15 of the present embodiment includes an optical element 16 having negative refractive power, and a high-speed Z scan driving section 17 that moves the optical element 16 along the optical axis. A lens 21 is provided between the optical element 16 and the XY scan unit 25. The laser beam through the high-speed Z scan unit 15 is guided into the XY scan unit 25 through the lens 21.

The convergence position of the pulsed laser beam moves in Z direction as the optical element 16 disposed on the optical path moves along the optical axis. The ophthalmic laser surgical apparatus 1 can thus scan the convergence position in Z direction by driving the high-speed Z scan driving section 17 and moving the optical element 16 under the control of the control unit. The high-speed Z scan unit 15 of the present embodiment can scan the convergence position in Z direction faster than a Z scan unit 44 (described later). With the high-speed Z scan unit 15, the control unit can thus more finely adjust the convergence position in Z direction. For example, for improved convergence accuracy, the control unit may be adapted to drive the high-speed Z control unit 15 according to the tilt of patient's eye E. It is also possible to drive the high-speed Z control unit 15 according to the XY scan performed by the XY scan unit 25, so that the convergence position errors caused in Z direction by the XY scan can be reduced.

The XY scan unit 25 scans the pulsed laser beam on the XY plane that crosses the optical axis. In the present embodiment, the XY scan unit 25 includes an X deflecting device 26 and a Y deflecting device 27. The X deflecting device 26 deflects the pulsed laser beam from the laser light source 10 to scan in X direction. The Y deflecting device 27 scans in Y direction by deflecting the pulsed laser beam scanned in X direction by the X deflecting device 26. The X deflecting device 26 and the Y deflecting device 27 both use a galvano mirror in the present embodiment. However, other light scanning devices (for example, such as a polygon mirror, and an acoustic optical modulator (AOM)) also may be used for at least one of the X deflecting device 26 and the Y deflecting device 27.

The configuration of the XY scan unit 25 of First Embodiment is described below in greater detail with reference to FIG. 2. As an example, the XY scan unit 25 of First Embodiment uses three galvano mirrors. Specifically, the X deflecting device 26 of First Embodiment includes a first X deflecting device 28 and a second X deflecting device 29. The first X deflecting device 28 scans the pulsed laser beam in X direction upon the beam being incident from the upstream side of the optical path (through the lens 21 in the present embodiment). The rotational axis line of the second X deflecting device 29 is parallel to the rotational axis line of the first X deflecting device 28. The pulsed laser beam scanned in X direction by the first X deflecting device 28 is further scanned in X direction by the second X deflecting device 29. As illustrated in FIG. 2, the control unit controls the amount of scan by the second X deflecting device 29 according to the amount of the scan performed by the first X deflecting device 28, so that the pulsed laser beam is incident on a predetermined position of the Y deflecting device 27 (the center of the scan surface of the mirror in the present embodiment). Specifically, the principal ray of the pulsed laser beam is incident on the predetermined position of the Y deflecting device 27, irrespective of the X-direction scan amount. In this way, the ophthalmic laser surgical apparatus 1 will not be affected by various effects due to changes in the incident position of the pulsed laser beam on the Y deflecting device 27. In First Embodiment, the center of the scan surface of the Y deflecting device 27 is the pivot point where the principal rays of all the pulsed laser beams scanned by the XY scan unit 27 pass through.

Figure 2:
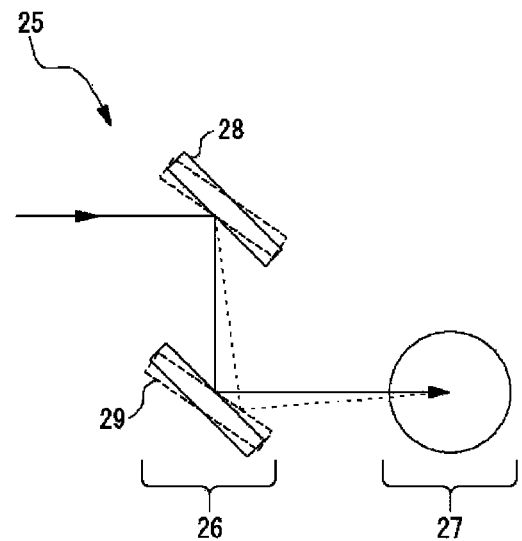
FIG. 2 is a diagram representing the configuration of the XY scan unit of First Embodiment.

As illustrated in FIG. 1, a relay unit 30 is provided between the XY scan unit 25 and the objective lens 35. The relay unit 30 of the present embodiment is a Keplerian relay optical system. The function of the Keplerian relay optical system can be realized by two lenses, even when the system is configured from three or more optical members. Accordingly, the relay unit 30 in FIG. 1 is shown as a two-lens unit. The other Keplerian relay optical systems described below are also shown as two-lens systems. The relay unit 30 includes an upstream relay optical element 31 and a downstream relay optical element 32, and conjugates the pivot point of the XY scan unit 25 (pivot point P at the center of the scan surface of the Y deflecting device 27 in First Embodiment) to the primary focal point of the objective lens 35 (described later).

Figure 3:
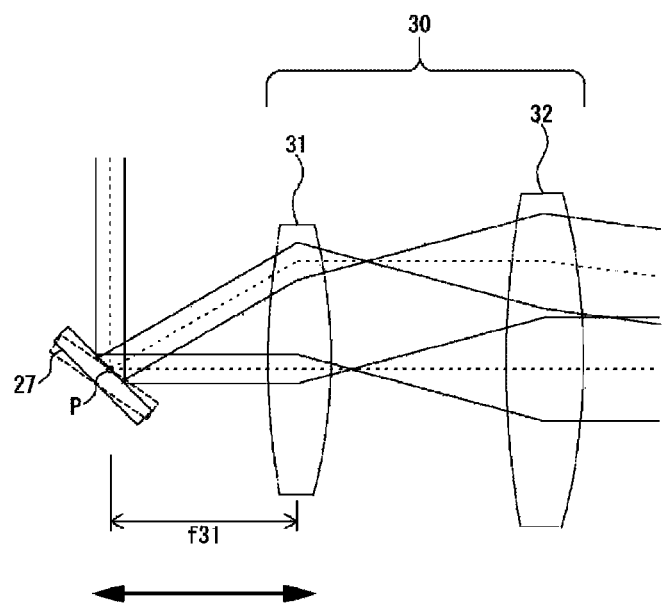
FIG. 3 is an explanatory diagram explaining the configurations of the Y scan unit and the upstream relay optical element of First Embodiment.

As illustrated in FIG. 3, the positions of the upstream relay optical element 31 and the XY scan unit 25 are maintained so that the primary focal point of the upstream relay optical element 31 is on the pivot point P of the XY scan unit 25. Specifically, the distance between the upstream relay optical element 31 and the pivot point P is the same as the focal length f31 of the upstream relay optical element 31. In this way, the pulsed laser beam emerging from the upstream relay optical element 31 can remain telecentric.

The objective lens 35 is disposed downstream of the downstream relay optical element 32 of the relay unit 30 on the optical path. In other words, the principal plane of the objective lens 35 is positioned on the downstream side of the principal plane of the downstream relay optical element 32 on the optical path. The pulsed laser beam through the objective lens 35 converges into the tissue of patient's eye E through an eyeball fixing interface 37. Though not detailed in the figure, the eyeball fixing interface 37 has a suction ring and a cup. The suction ring is placed under reduced pressure with a suction pump or the like. Under applied reduced pressure, the suction ring sucks and fixes the anterior part of patient's eye E. The cup covers the peripheral region of the anterior part of the eye. During a surgery, the cup is filled with a liquid having the same levels of refractive index as the refractive index of the cornea. In this way, the pulsed laser beam undergoes little refraction at the cornea and other parts of the eye, and the accuracy of the convergence position improves. The configuration of the eyeball fixing interface 37 may be appropriately varied. A contact lens or the like may be fitted to patient's eye E. The ophthalmic laser surgical apparatus 1 may be used to perform a surgery without using the eyeball fixing interface 37 or the like.

A dichroic mirror 38 is provided between the objective lens 35 and the downstream relay optical element 32 on the optical path. In the present embodiment, the dichroic mirror 38 reflects most of the pulsed laser beam from the laser light source 10, and most of the aiming beam from the aiming light source 11, and passes most of the light from an observation unit 40 and an OCT unit 41 (described later). These light beams can thus have the same optical axis. When the light from the observation unit 40 and the OCT unit 41 is made to have the same optical axis as the pulsed laser beam, the same optical axis may occur at different locations.

In First Embodiment, the downstream relay optical element 32 of the relay unit 30 represents the refractive optical element (hereinafter, "upstream element of the objective lens 35") that is closest to the objective lens 35 from among the optical elements disposed on the upstream side of the objective lens 35 on the optical path. In First Embodiment, the distance from the principal plane of the upstream element of the objective lens 35 to the principal plane of the objective lens 35 is equal to the sum of the focal length of the upstream element of the objective lens 35 and the focal length of the objective lens 35. Specifically, the secondary (posterior/back) focal point of the downstream relay optical element 32 lies on the primary focal point of the objective lens 35. In the present embodiment, the downstream relay optical element 32 and the objective lens 35 are fixed in position on the optical path.

As described above, in First Embodiment, the relay unit 30 conjugates the pivot point P of the XY scan unit 25 to the primary focal point of the objective lens 35. Accordingly, the principal rays of all the pulsed laser beams scanned by the XY scan unit 25 pass through the primary focal point of the objective lens 35. In the present embodiment, the dichroic mirror 38 is positioned at the primary focal point of the objective lens 35 (at the secondary focal point of the downstream relay optical element 32).

The focal length for specifying the primary focal point of the objective lens 35 may be the focal length of only the objective lens 35, or the focal length of an optical element including the objective lens 35 and the eyeball fixing interface 37. The same holds when considering the principal plane of the objective lens 35. Specifically, the term "objective lens" as used herein may mean an optical element that includes the eyeball fixing interface 37.

The observation unit 40 takes a frontal view of patient's eye E. The observation unit 40 of the present embodiment can capture the patient's eye E under visible light or infrared light, and display the captured image on a monitor (not illustrated). An operator can then observe the frontal view of patient's eye E through the monitor.

The OCT unit 41 takes a tomographic image of the tissue of patient's eye E. As an example, the OCT unit 41 of the present embodiment includes a light source, a light splitter, a reference optical system, a scan unit, and a detector. The light source emits light for taking a tomographic image. The light splitter splits the emitted light from the light source into reference light and measurement light. The reference light is incident on the reference optical system, and the measurement light is incident on the scan unit. The reference optical system is configured to vary the optical path length difference between the measurement light and the reference light. The scan unit two-dimensionally scans the measurement light on tissue. The detector detects the interference state of the measurement light reflected by tissue, and the reference light that has entered the reference optical system. The ophthalmic laser surgical apparatus 1 scans the measurement light, and detects the interference state of the reflected measurement light and the interference light to obtain depth-wise tissue information. The depth information is then used to obtain a tomographic image of the tissue. In the ophthalmic laser surgical apparatus 1 of the present embodiment, the target position where the pulsed laser beam is converged is correlated to the tomographic image of patient's eye E. In this way, the ophthalmic laser surgical apparatus 1, by using the tomographic image, can create data for controlling the irradiation and scan operations of the pulsed laser beam. The OCT unit 41 may have various configurations. For example, the OCT unit 41 may be realized by any of SS-OCT, SD-OCT, and TD-OCT. The ophthalmic laser surgical apparatus 1 may capture a tomographic image by using a technique other than light interference. The OCT unit 41 may be omitted when the target position can be determined without using a tomographic image (for example, when treating only a flattened cornea).

The dichroic mirror 42 provides the same optical axis for the light from the observation unit 40 and the OCT unit 41. The light from the dichroic mirror 42 falls on the dichroic mirror 38, and is made to have the same optical axis as the pulsed laser beam from the laser light source 10.

The Z scan unit 44 scans the convergence position of the pulsed laser beam in Z direction along the optical axis. Specifically, the Z scan unit 44 receives the pulsed laser beam from the laser light source 10, and scans the convergence position of the pulsed laser beam in Z direction. In First Embodiment, the upstream relay optical element 31 is an optical element with refractive power, and is provided downstream of the X deflecting device 26 and the Y deflecting device 27 of the XY scan unit 25 on the optical path. The upstream relay optical element 31 of First Embodiment is a light guiding optical element through which the pulsed laser beam emerges from the Z scan unit 44 toward the downstream side of the optical path. With the objective lens 35 fixed in position on the optical path, the ophthalmic laser surgical apparatus 1 varies the optical path length between the upstream relay optical element 31 (light guiding optical element) and the objective lens 35 to scan the convergence position in Z direction. In other words, the ophthalmic laser surgical apparatus 1 varies the distance between the principal planes of the upstream relay optical element 31 and the objective lens 35 on the optical path to scan the convergence position in Z direction.

As an example, the Z scan unit 44 of First Embodiment moves at least some of or all of the constituting elements of the XY scan unit 25 along the optical axis to scan the convergence position in Z direction. Specifically, the Z scan unit 44 in First Embodiment moves the optical unit including the XY scan unit 25 and the upstream relay optical element 31 along the optical axis to vary the optical path length between the upstream relay optical element 31 and the objective lens 35. More specifically, the Z scan unit 44 in First Embodiment moves the high-speed Z scan unit 15 and the lens 21 along the optical axis, together with the XY scan unit 25 and the upstream relay optical element 31.

As described above, the ophthalmic laser surgical apparatus 1 of First Embodiment varies the optical path length between the light guiding optical element provided downstream of at least one of the deflecting devices 26 and 27 (both the deflecting device 26 and the deflecting device 27 in First Embodiment) on the optical path and the objective lens 35 with the objective lens 35 being fixed in position on the optical path (the ophthalmic laser surgical apparatus 1 varies the optical path length between the principal planes of the light guiding optical element and the objective lens 35). In other words, the ophthalmic laser surgical apparatus 1 of First Embodiment moves at least some of or all of the constituting elements of the XY scan unit 25 (all of the constituting elements in First Embodiment) along the optical axis to scan the convergence position of the pulsed laser beam in Z direction. Specifically, the Z scan unit 44 of First Embodiment moves at least some of or all of the constituting elements of the XY scan unit 25, and the refractive optical element (the upstream relay optical element 31 in First Embodiment) along the optical axis. The optical element forms a laser beam waist image at a finite distance. The optical element forms a conjugate point of the convergence position formed by the objective lens 35. In this way, the ophthalmic laser surgical apparatus 1 can appropriately scan the convergence position of the pulsed laser beam. The following specifically describes some of the advantages of using the optical system of the ophthalmic laser surgical apparatus 1 of the present embodiment, using some examples.

As an example, it is considered possible to scan the convergence position in Z direction by moving the optical member disposed upstream of the XY scan unit 25 along the optical axis direction, instead of using the Z scan unit 44 of First Embodiment. Specifically, it may be possible to move the expander disposed upstream of the XY scan unit 25. It also may be possible to perform the Z scan by moving a mirror (optical path length varying section) provided upstream of the XY scan unit 25 on the optical path for reflecting the pulsed laser beam. In this case, the displacement of the convergence position in Z direction relative to the displacement of the optical member is affected by the optical system disposed downstream of the moved optical member. This may necessitate the optical member to move by a large distance to ensure a sufficient displacement for the convergence position.

The following describes this problem by using an exemplary variation of the configuration shown in FIG. 1. It is assumed here that the Z scan is performed only with the high-speed Z scan unit 15 without using the Z scan unit 44 in First Embodiment represented in FIG. 1. When the focal lengths of the upstream relay optical element 31 and the downstream relay optical element 32 are f31 and f32, respectively, the lateral magnification of the relay unit 30 downstream of the XY scan unit 25 can be represented by f32/f31. Here, the objective lens 35 generally needs to have a sufficiently long focal length in order to provide a sufficient numerical aperture NA for the pulsed laser beam emerging from the objective lens 35, and maintain an appropriate distance between the objective lens 35 and patient's eye E. On the other hand, because of the high-speed driving requirement of the XY scan unit 25, the galvano mirror used for the XY scan unit 25 is often much smaller in size than the entrance pupil of the objective lens 35. This tends to increase the lateral magnification f32/f31 of the relay unit 30. When the Z scan is performed solely with the high-speed Z scan unit 15, the displacement of the high-speed Z scan unit 15 needed to move the focal position by unit distance in Z direction is proportional to the axial magnification (the square of the lateral magnification) of the relay unit 30. Accordingly, any restriction imposed by the relay unit 30 may make it difficult to provide a smaller displacement for the high-speed Z scan unit 15. Similarly, any restriction imposed by the upstream optical element of the XY scan unit 25 may affect an attempt to reduce the displacement of the high-speed Z scan unit 15. When the Z scan is performed on the upstream side of the XY scan unit 25, the XY scan unit 25 needs to XY scan the pulsed laser beam emerging through the high-speed Z scan unit 15. This makes it difficult to reduce the size of the XY scan unit 25. This problem also occurs in a Z scan performed by moving the mirror.

It may be possible to reduce the displacement of the optical member by moving the optical member disposed downstream of the XY scan unit 25 (for example, the downstream relay optical element 32, or the objective lens 35) along the optical axis. However, in this case, the Z scan unit also needs to appropriately scan the pulsed laser beam scanned off-axis by the XY scan unit 25, and may require a complicated design. Further, when performing the Z scan by moving the objective lens 35 or the like, the Z scan tends to cause aberration as the scan proceeds. This may lead to problems such as complicating the optical system design. Further, in order to move the objective lens 35, the eyeball fixing interface 37 needs to be designed in a manner allowing the objective lens 35 to be movable.

In contrast, the ophthalmic laser surgical apparatus 1 of First Embodiment varies the optical path length between the light guiding optical element disposed downstream of at least one of the deflecting devices 26 and 27 on the optical path and the objective lens 35 with the objective lens 35 being fixed in position on the optical path. In other words, the ophthalmic laser surgical apparatus 1 of First Embodiment scans the convergence position of the pulsed laser beam in Z direction by moving at least some of or all of the constituting elements of the XY scan unit 25 (all of the constituting elements in First Embodiment) along the optical axis. In this way, the effect of the optical system disposed downstream of the Z scan unit 44 becomes smaller than when the Z scan is performed on the upstream side of the XY scan unit 25. It also becomes easier to reduce the size of the XY scan unit 25. Further, in contrast to performing the Z scan on the downstream side of the XY scan unit 25, there is less need to make changes, for example, such as design changes intended to more appropriately perform the Z scan for the XY scanned pulsed laser beam. There is accordingly no need to consider the effects of moving the objective lens 35. The ophthalmic laser surgical apparatus 1 can thus more appropriately scan the convergence position of the pulsed laser beam.

In First Embodiment, the positions of the optical elements disposed downstream of the Z scan unit 44 on the optical path (specifically, the downstream relay optical element 32, the dichroic mirror 38, and the objective lens 35) remain constant on the optical path, regardless of the driving of the Z scan unit 44. In First Embodiment, the XY scan unit 25 and the upstream relay optical element 31 have a fixed positional relationship at least while the tissue is being irradiated with the pulsed laser beam, even when the Z scan is performed. This makes it easier to control the scan of the convergence position. Further, the primary focal point of the upstream relay optical element 31 (light guiding optical element) lies on the pivot point of the XY scan unit 25. In this case, the pulsed laser beam emerging from the light guiding optical element can remain telecentric even when the focal position is Z scanned by the Z scan unit 44. The emission angle of the pulsed laser beam from the objective lens 35 can thus remain constant irrespective of the Z scan. In other words, a Z scan performed on the downstream side of the deflecting devices 26 and 27 has the possibility of changing the conjugate relationship as the Z scan proceeds, and varying the emission angle of the pulsed laser beam. In contrast, the ophthalmic laser surgical apparatus 1 of First Embodiment can appropriately scan the convergence position in Z direction on the downstream side of the deflecting devices 26 and 27 while maintaining the conjugate relationship and fixing the emission angle of the pulsed laser beam. This makes it even easier to control the scan of the convergence position. For example, it becomes easier to control the off-axis scan of the pulsed laser beam. It also becomes easier to control the irradiation position of the pulsed laser beam based on an OCT image (for example, creation of control data for controlling the XY scan unit 25 and the Z scan unit 44).

Further, in First Embodiment, the principal rays of all the pulsed laser beams scanned by the XY scan unit 25 pass through the primary focal point of the objective lens 35. In this case, the objective lens 35 can maintain its posterior telecentric performance even with the Z scan of the convergence position. In other words, the emission angle of the pulsed laser beam emerging from the objective lens 35 toward patient's eye E can remain parallel. This makes it even easier to control the scan of the convergence position.

In First Embodiment, the distance from the principal plane of the downstream relay optical element 32 in the relay unit 30 to the principal plane of the objective lens 35 is equal to the sum of the focal lengths of these elements. In this case, the numerical aperture NA of the pulsed laser beam emerging from the objective lens 35 is maintained even in the presence of a Z scan performed by the Z scan unit 44. By assuming that the effect of aberration is negligible, the spot size becomes constant with the maintained constant numerical aperture NA, regardless of the scan amount in Z direction.

The ophthalmic laser surgical apparatus 1 of First Embodiment moves the optical unit including the XY scan unit 25 and the upstream relay optical element 31 of the relay unit 30 along the optical axis. In this case, the XY scan unit 25 can be realized without providing a relay unit between the X deflecting device 26 and the Y deflecting device 27. With the absence of a relay unit between the X deflecting device 26 and the Y deflecting device 27, the configuration can be more simplified than with a relay unit, and the effect of aberration can be reduced. There is also no need to make design changes intended to appropriately perform a Z scan for the XY scanned laser.

In First Embodiment, the XY scan unit 25 includes the first X deflecting device 28, the second X deflecting device 29, and the Y deflecting device 27. The pulsed laser beam scanned in X direction by the first X deflecting device 28 and the second X deflecting device 29 is incident on the predetermined position of the Y deflecting device 27. Here, the Y scan takes place at the predetermined position of the Y deflecting device 27, regardless of the scan amount in X direction. This further improves the scan accuracy of the convergence position.

In First Embodiment, the high-speed Z scan unit (second Z scan unit) 15 is provided between the laser light source 10 and the XY scan unit 25 on the optical path. The accuracy of treatment improves with the provision of more than one Z scan unit. As an example, the high-speed Z scan unit 15 of the present embodiment Z scans the convergence position of the pulsed laser beam faster than the Z scan unit 44. In this way, the ophthalmic laser surgical apparatus 1 can Z scan the convergence position at high speed in a manner that depends on various factors (for example, any of the tilt of the eye ball, and the field curvature due to the XY scan) during the treatment with the pulsed laser beam.

In First Embodiment, the zoom expander 13 is provided between the laser light source 10 and the XY scan unit 25 on the optical path. The zoom expander 13 varies the beam diameter of the pulsed laser beam. By varying the beam diameter with the zoom expander 13, the ophthalmic laser surgical apparatus 1 can adjust the numerical aperture NA of the pulsed laser beam emerging from the objective lens 35. The zoom expander 13 of the present embodiment is disposed upstream of the XY scan unit 25, and does not need to accommodate the pulsed laser beam scanned off-axis.

Second Embodiment

Figure 4:
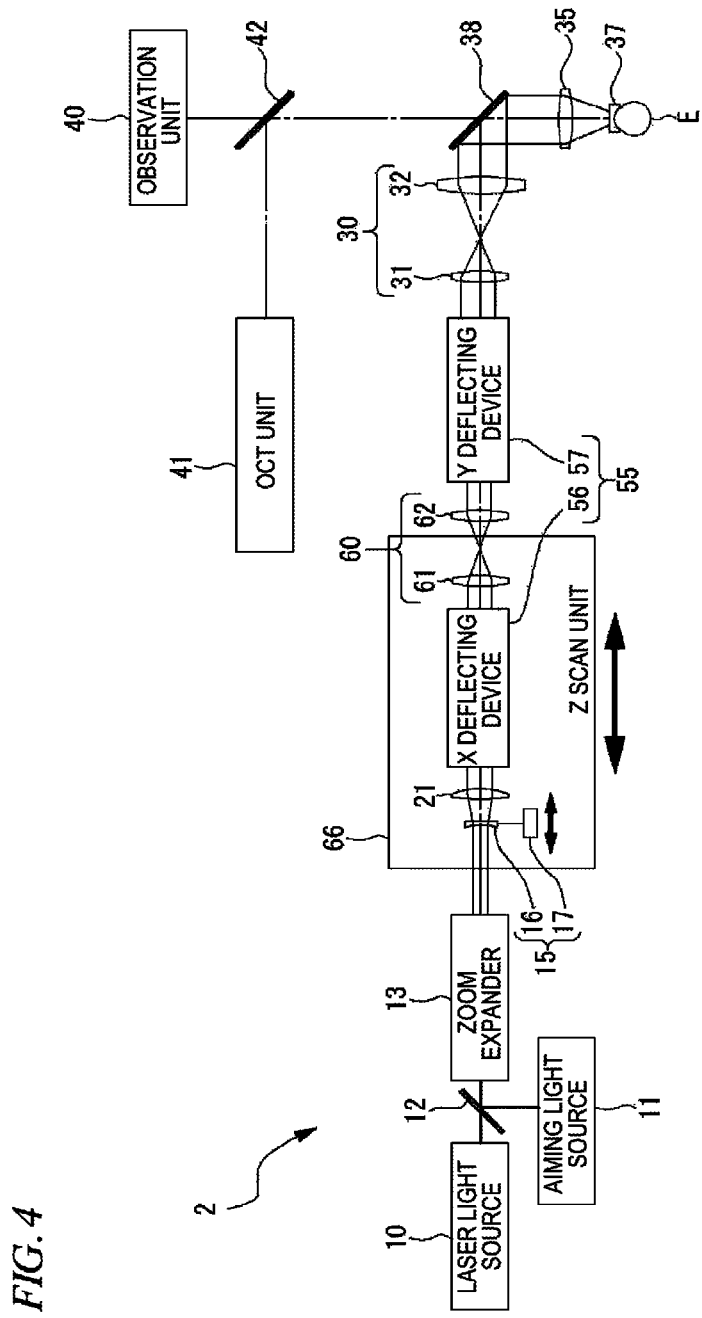
FIG. 4 is a diagram representing the configuration of the ophthalmic laser surgical apparatus of Second Embodiment.

Second Embodiment as another illustrative embodiment according to the present disclosure different from First Embodiment will be described below with reference to FIG. 4. Second Embodiment shares some common features with First Embodiment, but differs from First Embodiment in some respects, for example, in the configurations of an XY scan unit 55 and a Z scan unit 66. Accordingly, such common features are given the same reference numerals used in First Embodiment, and explanations thereof will be omitted or simplified. Second Embodiment is, for example, an ophthalmic laser surgical apparatus 2 that can treat both the cornea and the crystalline lens of patient's eye E as with the case of First Embodiment.

The ophthalmic laser surgical apparatus 2 of Second Embodiment includes a laser light source 10, an aiming light source 11, a dichroic mirror 12, a zoom expander 13, a high-speed Z scan unit 15, and a lens 21. The configuration from the laser light source 10 to the lens 21 may be the same configuration described in First Embodiment.

The XY scan unit 55 of Second Embodiment includes an X deflecting device 56, a Y deflecting device 57, and an XY relay unit 60. The X deflecting device 56 performs an X scan for the incident pulsed laser beam from the lens 21. The Y deflecting device 57 performs a Y scan for the incident pulsed laser beam from the X deflecting device 56. As an example, the X deflecting device 56 and the Y deflecting device 57 are each realized by a single galvano mirror in Second Embodiment. It is possible, however, to use other light scanning devices. More than one device (for example, two galvano mirrors) may be used for at least one of the X deflecting device 56 and the Y deflecting device 57.

The XY relay unit 60 is provided between the X deflecting device 56 and the Y deflecting device 57. The XY relay unit 60 includes an upstream XY relay optical element 61, and a downstream XY relay optical element 62 provided downstream of the upstream XY relay optical element 61. The XY relay unit 60 is a Keplerian relay optical system, relaying the X deflecting device 56 to the Y deflecting device 57. Specifically, the XY relay unit 60 conjugates the scan center of the X deflecting device 56 to the scan center of the Y deflecting device 57. The positional relationship between the upstream XY relay optical element 61 and the X deflecting device 56 is maintained in such a manner that the primary (anterior) focal point of the upstream XY relay optical element 61 is on the scan center of the X deflecting device 56. The pulsed laser beam emerging from the upstream XY relay optical element 61 can thus remain telecentric. In Second Embodiment, the downstream XY relay optical element 62 and the Y deflecting device 57 have a fixed positional relationship. Specifically, the positional relationship between the downstream XY relay optical element 62 and the Y deflecting device 57 is maintained in such a manner that the secondary (posterior) focal point of the downstream XY relay optical element 62 is on the scan center of the Y deflecting device 57.

A relay unit 30, a dichroic mirror 38, and an objective lens 35 are provided in this order on the downstream side of the XY scan unit 55 on the optical path. The relay unit 30, the dichroic mirror 38, and the objective lens 35 may have the same configurations described in First Embodiment. Specifically, the positional relationship between the upstream relay optical element 31 and the Y deflecting device 57 is maintained in such a manner that the primary focal point of the upstream relay optical element 31 is on the pivot point of the Y deflecting device 57 as with the case of First Embodiment. The distance from the principal plane of the upstream element of the objective lens 35 (the downstream relay optical element 32 in Second Embodiment) to the principal plane of the objective lens 35 on the optical path is equal to the sum of the focal length of the upstream element of the objective lens 35 and the focal length of the objective lens 35. The principal rays of all the pulsed laser beams scanned by the XY scan unit 55 pass through the primary focal point of the objective lens 35. However, unlike First Embodiment, the upstream relay optical system 31 of the relay unit 30 does not move along the optical axis in Second Embodiment, as will be described later in detail.

In Second Embodiment, the distance from the principal plane of the upstream relay optical element 31 to the principal plane of the downstream relay optical element 32 of the relay unit 30 on the optical path is equal to the sum of the focal length of the upstream relay optical element 31 and the focal length of the downstream relay optical element 32. The distance from the principal plane of the upstream relay optical element 31 to the principal plane of the downstream XY relay optical element 62 on the optical path is equal to the sum of the focal length of the upstream relay optical element 31 and the focal length of the downstream XY relay optical element 62. In this case, the numerical aperture NA of the pulsed laser beam emerging from the objective lens 35 is maintained even in the presence of a Z scan performed by the Z scan unit 66.

Second Embodiment also may include an observation unit 40 and an OCT unit 41. The configurations of components such as the observation unit 40, the OCT unit 41, and the dichroic mirrors 38 and 42 may be the same or different from those described in First Embodiment.

The Z scan unit 66 scans the convergence position in Z direction by varying the optical path length between the light guiding optical element and the objective lens 35 with the objective lens 35 being fixed in position on the optical path, as in First Embodiment. Specifically, the Z scan unit 66 of Second Embodiment scans the convergence position of the pulsed laser beam in Z direction by moving at least a part of the XY scan unit 55 along the optical axis in the same manner as described in First Embodiment. However, in Second Embodiment, the upstream XY relay optical element 61 serves as the light guiding optical element. The Z scan unit 66 of Second Embodiment moves the optical unit including the X deflecting device 56 and the upstream XY relay optical element 61 of the XY relay unit 60 along the optical axis. The Z scan unit 66 of Second Embodiment does not move the downstream XY relay optical element 62, the Y deflecting device 57, the relay unit 30, and the objective lens 35. The Z scan unit 66 of Second Embodiment moves the high-speed Z scan unit 15 and the lens 21 along the optical axis, together with the X deflecting device 56 and the upstream XY relay optical element 61.

In Second Embodiment, the upstream XY relay optical element 61 represents the optical element that is the most downstream of the optical elements with refractive power on the optical path of the Z scan unit 66. The upstream XY relay optical element 61 thus serves as a light guiding optical element through which the pulsed laser beam emerges out of the Z scan unit 66. The primary focal point of the upstream XY relay optical element 61 lies on the pivot point of the X scan unit 56.

As described above, the ophthalmic laser surgical apparatus 2 of Second Embodiment varies the optical path length between the light guiding optical element provided downstream of at least one of the deflecting devices 56 and 57 (the X deflecting device 56 in Second Embodiment) on the optical path and the objective lens 35 with the objective lens 35 being fixed in position on the optical path, as with the case of the ophthalmic laser surgical apparatus 1 of First Embodiment. In this way, the effect of the optical system disposed downstream of the Z scan unit 66 becomes smaller than when the Z scan is performed on the upstream side of the XY scan unit 55. It also becomes easier to reduce the size of the XY scan unit 55. There is also no need to consider the effects of moving the objective lens 35. The ophthalmic laser surgical apparatus 2 can thus appropriately scan the convergence position of the pulsed laser beam.

In other words, the ophthalmic laser surgical apparatus 2 of Second Embodiment scans the convergence position of the pulsed laser beam in Z direction by moving at least a part of the XY scan unit 66 along the optical axis, as with the case of the ophthalmic laser surgical apparatus 1 of First Embodiment. Specifically, the Z scan unit 66 of Second Embodiment moves at least a part of the XY scan unit 55 and the optical element having refractive power (the upstream XY relay optical element 61 in Second Embodiment) along the optical axis. The ophthalmic laser surgical apparatus 2 can thus appropriately scan the convergence position of the pulsed laser beam with a simpler configuration.

Specifically, the Z scan unit 66 of Second Embodiment moves the convergence position in Z direction by moving the optical unit including the X deflecting device 56 and the upstream XY relay optical element 61 (light guiding optical element) along the optical axis. In this way, the ophthalmic laser surgical apparatus 2 can perform the Z scan without moving the Y deflecting device 57. The focal length of the lens 21 disposed immediately in the front of the X deflecting device 56 can be confined within the distance that does not exceed the X deflecting device 56. This makes it easier to decrease the focal length of the lens 21.

In Second Embodiment, the positions of the optical elements disposed downstream of the Z scan unit 66 on the optical path (specifically, the downstream XY relay optical element 62, the Y deflecting device 57, the relay unit 30, and the objective lens 35) remain constant on the optical path, regardless of the driving of the Z scan unit 66. Further, in Second Embodiment, the X deflecting device 56 and the upstream XY relay optical element 61 have a fixed positional relationship even when the Z scan is performed, as with the case in First Embodiment. Further, the primary focal point of the upstream XY relay optical element 61 (light guiding optical element) lies on the pivot point of the X deflecting device 56. In this case, the pulsed laser beam emerging from the light guiding optical element can remain telecentric. Further, the emission angle of the pulsed laser beam from the objective lens 35 can remain constant with the maintained conjugate relationship on the downstream side of the Z scan unit 66, irrespective of the Z scan. This makes it easier to control the scan of the convergence position. The ophthalmic laser surgical apparatus 2 of Second Embodiment shares some common features with the ophthalmic laser surgical apparatus 1 of First Embodiment, and can exhibit at least some of the effects described in First Embodiment.

Third Embodiment

Figure 5:
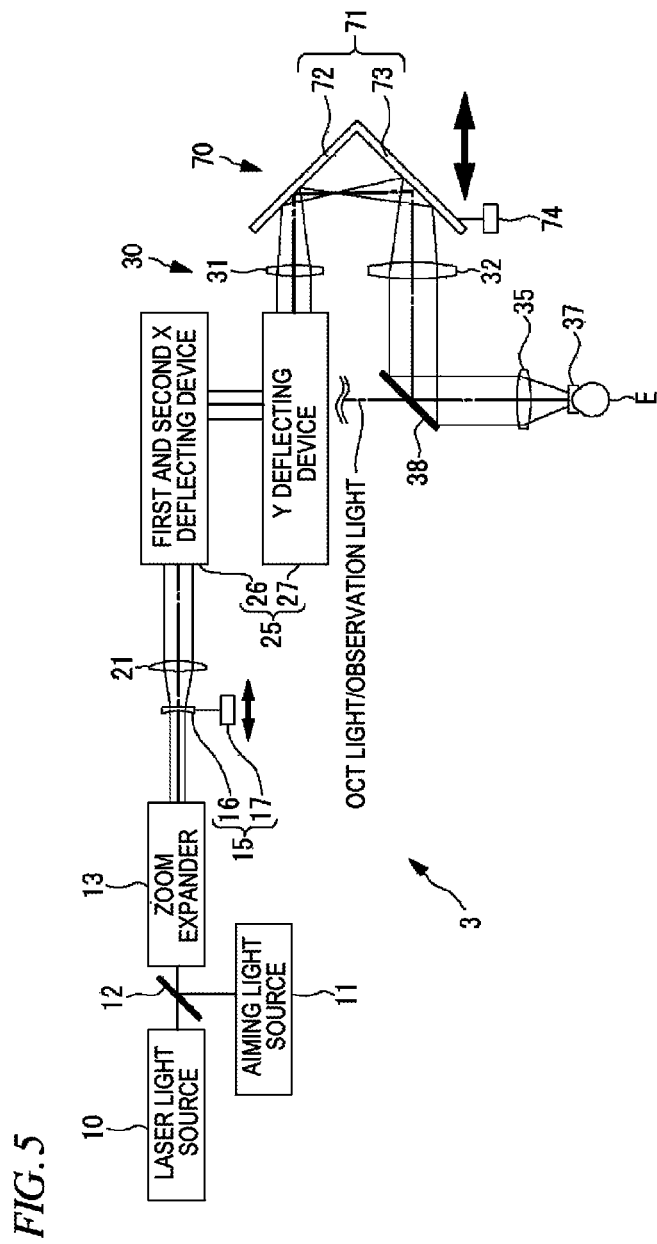
FIG. 5 is a diagram representing the configuration of the ophthalmic laser surgical apparatus of Third Embodiment.

Third Embodiment of the present invention is described below with reference to FIG. 5. Third Embodiment differs from First Embodiment in that a reflecting unit 71 is moved to perform the Z scan, but shares some common features with First Embodiment. Accordingly, such common features are given the same reference numerals used in First Embodiment, and explanations thereof will be omitted or simplified.

The ophthalmic laser surgical apparatus 3 of Third Embodiment includes a laser light source 10, an aiming light source 11, a dichroic mirror 12, a zoom expander 13, a high-speed Z scan unit 15, a lens 21, and an XY scan unit 25. The configuration from the laser light source 10 to the XY scan unit 25 may be the same configuration described in First Embodiment.

A Keplerian relay unit 30 is provided downstream of the XY scan unit 25 on the optical path. The relay unit 30 includes an upstream relay optical element 31 and a downstream relay optical element 32. The primary focal point of the upstream relay optical element 31 lies on the pivot point of the XY scan unit 25. The pulsed laser beam emerging from the upstream relay optical element 31 can thus remain telecentric. The objective lens 35 is disposed on the downstream side of the downstream relay optical element 32. The relay unit 30 conjugates the pivot point of the XY scan unit 25 to the primary focal point of the objective lens 35. Accordingly, the principal rays of all the pulsed laser beams scanned by the XY scan unit 25 pass through the primary focal point of the objective lens 35. The distance from the principal plane of the downstream relay optical element 32 to the principal plane of the objective lens 35 is equal to the sum of the focal lengths of these elements. Third Embodiment may include an observation unit 40 and an OCT unit 41, though not shown in FIG. 5. The configurations of components such as the observation unit 40, the OCT unit 41, and the dichroic mirrors 38 and 42 may be the same or different from those described in First Embodiment.

In Third Embodiment, a Z scan unit 70 is provided between the upstream relay optical element 31 and the downstream relay optical element 32 of the relay unit 30. The Z scan unit 70 of Third Embodiment includes the reflecting unit 71 and a Z scan driving section 74.

The reflecting unit 71 is provided on the optical path between the upstream relay optical element 31 and the downstream relay optical element 32. As an example, the reflecting unit 71 of Third Embodiment uses mirrors that reflect the pulsed laser beam from the upstream relay optical element 31 into the downstream relay optical element 32. More specifically, the reflecting unit 71 of the present embodiment includes two reflectors 72 and 73. The reflector 72 reflects the incident pulsed laser beam from the upstream relay optical element 31 onto the reflector 73. The reflector 73 reflects the incident pulsed laser beam from the reflector 72 into the downstream relay optical element 32. The pulsed laser beam propagating is thus incident on the downstream relay optical element 32 in a direction 180° opposite from the direction of travel through the upstream relay optical element 31. In this way, the reflecting unit 71 can use as few reflectors as possible.

The Z scan driving section 74 moves the reflecting unit 71 to vary the optical path length between the light guiding optical element (the upstream relay optical element 31 in Third Embodiment) and the objective lens 35. This scans the convergence position of the pulsed laser beam in Z direction. Specifically, the Z scan driving section 74 of Third Embodiment moves the reflecting unit 71 in a direction parallel to the optical axis of the pulsed laser beam emerging from the upstream relay optical element 31 (the direction along the longer side of the paper in FIG. 5).

As described above, the ophthalmic laser surgical apparatus 3 of Third Embodiment, as in First and Second Embodiments, varies the optical path length between the light guiding optical element provided downstream of at least one of the deflecting devices 26 and 27 on the optical path (the upstream relay optical element 31 in Third Embodiment) and the objective lens 35 with the objective lens 35 being fixed in position on the optical path. The ophthalmic laser surgical apparatus 3 can thus appropriately scan the convergence position of the pulsed laser beam.

Specifically, the Z scan unit 70 of Third Embodiment includes the reflecting unit 71 and the Z scan driving section 74. The reflecting unit 71 is disposed on the optical path, and reflects the pulsed laser beam. The Z scan driving section 74 moves the reflecting unit 71 to vary the optical path length. In this way, fewer moving components are needed than when the Z scan is performed by moving the XY scan unit 25 itself. This makes it easier to simplify the mechanism needed for Z scan. More specifically, in Third Embodiment, the reflecting unit 71 is provided on the optical path between the upstream relay optical element 31 and the downstream relay optical element 32. In this way, the convergence position can be appropriately Z scanned with the reflecting unit 71. The ophthalmic laser surgical apparatus 3 of Third Embodiment shares some common features with the ophthalmic laser surgical apparatus 1 of First Embodiment, and can exhibit at least some of the effects described in First Embodiment.

Fourth Embodiment

Figure 6:
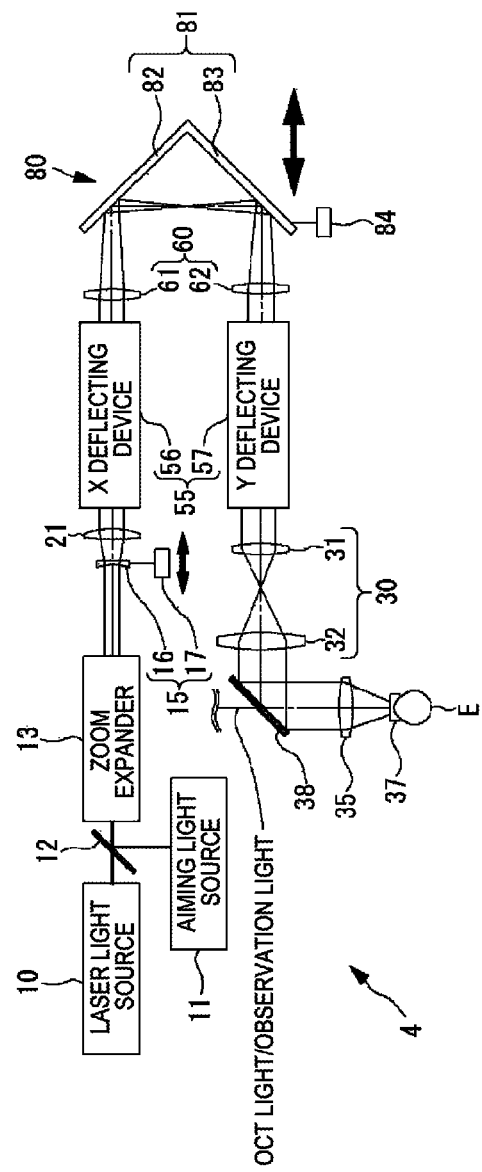
FIG. 6 is a diagram representing the configuration of the ophthalmic laser surgical apparatus of Fourth Embodiment.

Fourth Embodiment of the present invention is described below with reference to FIG. 6. Fourth Embodiment differs from Second Embodiment in that a reflecting unit 81 is moved to perform the Z scan, but shares some common features with Second Embodiment. Accordingly, such common features are given the same reference numerals used in Second Embodiment, and explanations thereof will be omitted or simplified.

The ophthalmic laser surgical apparatus 4 of Fourth Embodiment includes a laser light source 10, an aiming light source 11, a dichroic mirror 12, a zoom expander 13, a high-speed Z scan unit 15, a lens 21, and an X deflecting device 56. The configuration from the laser light source 10 to the X deflecting device 56 may be the same configuration described in Second Embodiment. The ophthalmic laser surgical apparatus 4 also includes a Y deflecting device 57, a relay unit 30, a dichroic mirror 38, and an objective lens 35. The configuration from the Y deflecting device 57 to the objective lens 35 may be the same configuration described in Second Embodiment. The observation unit 40 and the OCT unit 41 are omitted in the figure. Fourth Embodiment may adopt a configuration different from that of Second Embodiment.

An XY relay unit 60 is provided between the X deflecting device 56 and the Y deflecting device 57. In Fourth Embodiment, the XY relay unit 60 includes an upstream XY relay optical element 61, and a downstream XY relay optical element 62 positioned downstream of the upstream relay optical element 61. The primary focal point of the upstream XY relay optical element 6 lies on the scan center of the X deflecting device 56. The pulsed laser beam emerging from the upstream XY relay optical element 61 can thus remain telecentric. In Fourth Embodiment, the posterior focal point of the downstream XY relay optical element 62 lies on the scan center (pivot point) of the Y deflecting device 57.

In Fourth Embodiment, the primary focal point of the upstream relay optical element 31 lies on the pivot point of the Y deflecting device 57, as in Second Embodiment. The distance from the principal plane of the downstream relay optical element 32 to the principal plane of the objective lens 35 on the optical path is equal to the sum of the focal length of the downstream relay optical element 32 and the local length of the objective lens 35. The principal rays of all the pulsed laser beams scanned by the XY scan unit 55 pass through the primary focal point of the objective lens 35.

In Fourth Embodiment, a Z scan unit 80 is provided between the upstream XY relay optical element 61 and the downstream XY relay optical element 62 of the XY relay unit 60. The Z scan unit 80 of Fourth Embodiment includes a reflecting unit 81 and a Z scan driving section 84.

The reflecting unit 81 is provided on the optical path between the upstream XY relay optical element 61 and the downstream XY relay optical element 62. As an example, the reflecting unit 81 of Fourth Embodiment uses mirrors having the same configuration as that of the reflecting unit 71 of Third Embodiment. Specifically, in the reflecting unit 81 of Fourth Embodiment, the pulsed laser beam emerging from the upstream XY relay optical element 61 is reflected 180° by two reflectors 82 and 83. The pulsed laser beam from the reflecting unit 81 is incident on the downstream XY relay optical element 62.

The Z scan driving section 84 moves the reflecting unit 81 to vary the optical path length between the light guiding optical element (the upstream XY relay optical element 61 in Fourth Embodiment) and the objective lens 35. This scans the convergence position of the pulsed laser beam in Z direction. Specifically, the Z scan driving section 84 of Fourth Embodiment moves the reflecting unit 81 in a direction parallel to the optical axis of the pulsed laser beam emerging from the upstream XY relay optical element 61.

As described above, the ophthalmic laser surgical apparatus 4 of Fourth Embodiment, as in First to Third Embodiments, varies the optical path length between the light guiding optical element provided downstream of at least one of the deflecting devices 56 and 57 on the optical path (the upstream XY relay optical element 61 in Fourth Embodiment) and the objective lens 35. The ophthalmic laser surgical apparatus 4 can thus appropriately scan the convergence position of the pulsed laser beam.

Specifically, the Z scan unit 80 of Fourth Embodiment includes the reflecting unit 81 and the Z scan driving section 84. The reflecting unit 81 is disposed on the optical path, and reflects the pulsed laser beam. The Z scan driving section 84 moves the reflecting unit 81 to vary the optical path length. In this way, fewer components are needed than when the Z scan is performed by moving the XY scan unit 55 itself.

More specifically, in Fourth Embodiment, the reflecting unit 81 is provided on the optical path between the upstream XY relay optical element 61 and the downstream relay optical element 62. Here, the axial magnification of the optical system positioned downstream of the X deflecting device 56 can be adjusted by specifying the focal length of the upstream XY relay optical element 61, and the focal length of the downstream XY relay optical element 62. The displacement of the reflecting unit 81 needed to move the focal position by unit distance can thus be reduced by adjusting the axial magnification. Further, because the pulsed laser beam passes through the reflecting unit 81 before being scanned in Y direction, the size of the reflecting unit 81 can be made smaller than when the reflecting unit 81 is provided on the downstream side of the X deflecting device 56 and the Y deflecting device 57.

The ophthalmic laser surgical apparatus 4 of Fourth Embodiment shares some common features with the ophthalmic laser surgical apparatuses 1 to 3 of First to Third Embodiments, and can exhibit at least some of the effects described in First to Third Embodiments.

The present invention is not limited to the foregoing embodiments, and various modifications are possible. Referring to FIGS. 1 to 6, each optical element (for example, 16, 21, 31, 32, 35, 61, 62) is shown as a single optical member (for example, such as the lens). However, the optical element is not necessarily required to be configured from a single optical member, and may be configured from more than one optical member. The language "optical element A is positioned downstream of optical element B" as used in the descriptions of the foregoing embodiments means that the principal plane of the optical element A is on the downstream side of the principal plane of the optical element B. Accordingly, some of the optical members of the optical element A may be on the upstream side of at least some of the optical members of the optical element B in the foregoing examples.

The configurations shown in FIGS. 1 to 6 are simplified from the actual configurations, for convenience of explanation. As such, the configurations shown in the figures may include other optical members (for example, such as an optical member for bending the optical path). Further, the optical element may use various optical members, for example, such as a convex lens, a concave lens, a concave mirror, and a plane mirror, either individually or in combination.

In First and Second Embodiments, the Z scan units 44 and 66 move the optical element having positive refractive power (the upstream relay optical element 31 or the upstream XY relay optical element 61) along the optical axis with at least a part of the XY scan units 25 and 55. However, the Z scan units 44 and 66 may move optical elements having negative refractive power with at least a part of the XY scan units 25 and 55. The position of the optical element moved with at least a part of the XY scan units 25 and 55 is not limited to the positions described in First and Second Embodiments. For example, the optical element moved with at least a part of the XY scan units 25 and 55 by Z scan unit may be an optical element disposed upstream of the XY scan units 25 and 55.

The relay unit 30 and other such components may have different configurations. For example, referring to FIG. 4 (Second Embodiment) and FIG. 6 (Fourth Embodiment), the upstream relay optical element 31 and the downstream relay optical element 32 are provided between the Y deflecting device 57 and the objective lens 35. However, in Second and Fourth Embodiments, for example, the upstream relay optical element 31 of the relay unit 30 may be omitted, provided that the focal length of elements such as the downstream XY relay optical element 62 is adjusted to cause the pulsed laser beam to emerge from the Y deflecting device 57 as non-parallel rays. In this case, specifically, the primary focal point of the upstream XY relay optical element 61 is set at the scan center of the X deflecting device 56. The posterior focal point of the downstream XY relay optical element 62 is set at the scan center of the Y deflecting device 57. The scan center of the Y deflecting device 57 is conjugated to the primary focal point of the objective lens 35. This determines the convergence position as with the case of the Second and Fourth Embodiments. Likewise, the upstream relay optical element 31 of First and Third Embodiments, and the upstream XY relay optical element 61 of Second and Fourth Embodiments may be omitted. It is also possible to omit the downstream relay optical element 32, and the downstream XY relay optical element 62.

First to Fourth Embodiment described the case where the configurations including the laser light source 10, and the optical system for shining a laser beam on patient's eye E are integrated in the ophthalmic laser surgical apparatuses 1 to 4. It is, however, possible to incorporate the optical system and other configurations in the ophthalmic laser surgical apparatuses 1 to 4 as a module. Such a modular optical system may be represented as, for example, an optical system for use in an ophthalmic laser surgical apparatus for converging a pulsed laser beam in a tissue of a patient's eye for the treatment of the eye, the optical system including: an XY scan unit that includes at least one deflecting device for deflecting the pulsed laser beam emitted by a laser light source, and that uses the deflecting device to scan the pulsed laser beam in a direction crossing an optical axis; a light guiding optical element provided downstream of at least one of the deflecting devices of the XY scan unit on the optical path of the pulsed laser beam, the light guiding optical element having refractive power and guiding the pulsed laser beam toward the downstream side of the optical path; an objective lens that causes the pulsed laser beam through the XY scan unit and the light guiding optical element to converge in the tissue; and a Z scan unit that scans the convergence position of the pulsed laser beam in a Z direction along the optical axis by varying the optical path length between the light guiding optical element and the objective lens with the objective lens being fixed in position on the optical path.

The modular optical system also may be represented as an optical system for use in an ophthalmic laser surgical apparatus for converging a pulsed laser beam in a tissue of a patient's eye for the treatment of the eye, the optical system including: an XY scan unit that scans the pulsed laser beam from a laser light source in a direction crossing an optical axis; an objective lens disposed downstream of the XY scan unit on the optical path of the pulsed laser beam, and that converges the pulsed laser beam emerging from the XY scan unit; and a Z scan unit that scans the convergence position of the pulsed laser beam in a Z direction along the optical axis by moving at least a part of the XY scan unit along the optical axis.

First to Fourth Embodiments described the ophthalmic laser surgical apparatuses 1 to 4 that can be used for the treatment of both cornea and crystalline lens. However, the configurations described in the foregoing embodiments are also applicable to ophthalmic laser surgical apparatuses adapted to treat a specific site of patient's eye E (for example, only the cornea or the crystalline lens). A larger amount of Z scan is required in treatment of crystalline lens than in treatment of only the cornea. An even larger amount of Z scan is required in treatment of both cornea and crystalline lens than in treatment of only the crystalline lens. Performing an appropriate Z scan with a simple configuration becomes difficult as the amount of Z scan increases. However, the Z scan can be appropriately performed by using the techniques described in First to Fourth Embodiments. The techniques described in First to Fourth Embodiments become even more advantageous in treatment of crystalline lens, and in treatment of both crystalline lens and cornea. The ophthalmic laser surgical apparatuses 1 to 4 do not necessarily require a configuration for switching the optical path for treatment of cornea and for treatment of crystalline lens even when used to treat both crystalline lens and cornea.

In First Embodiment, the Z scan unit 44 moves the high-speed Z scan unit 15, the lens 21, the XY scan unit 25, and the upstream relay optical element 31 in optical axis direction. In Second Embodiment, the Z scan unit 66 moves the high-speed Z scan unit 15, the lens 21, the X deflecting device 56, and the upstream XY relay optical element 61 in optical axis direction. However, the configuration moved by the Z scan units 44 and 66 may be different from these. For example, in First and Second Embodiments, the high-speed Z scan unit 15 and the lens 21 may be excluded from the configuration moved by the Z scan units 44 and 46. The Z scan units 44 and 46 may also move other members, such as the zoom expander 13, in Z direction.

The ophthalmic laser surgical apparatuses 1 and 2 of First and Second Embodiments include the relay unit 30 on the upstream side of the objective lens 35. The ophthalmic laser surgical apparatuses 1 and 2 can thus appropriately converge a laser beam to the target position. The relay unit 30 allows the optical axes of the observation unit 40 and the OCT unit 41 to be easily combined with the optical axis of the pulsed laser beam. It is, however, possible to simplify the configuration by omitting the relay unit 30.

In the ophthalmic laser surgical apparatuses 1 to 4 of First to Fourth Embodiments, the high-speed Z scan unit 15 allows for Z scanning of the convergence position at high speed in a manner that depends on various factors. It is, however, possible to omit the high-speed Z scan unit 15. Further, contrary to what was described in First to Fourth Embodiments, the Z scan units 44, 66, 70, and 80 may have a faster scan rate than the Z scan unit 15. In this way, treatment accuracy also can easily improve compared to using a single Z scan unit. In the ophthalmic laser surgical apparatuses 1 to 4 of First to Fourth Embodiments, the zoom expander 13 can vary the beam diameter, and adjust the numerical aperture NA of the pulsed laser beam. It is, however, possible to omit the zoom expander 13. The high-speed Z scan unit 15 and the zoom expander 13 may be switched in position.

In First to Fourth Embodiments, the pulsed laser beam emerges from the objective lens 35 at a fixed angle (i.e., telecentricity is maintained). The ophthalmic laser surgical apparatuses 1 to 4 can thus easily scan the convergence position at high accuracy. However, the emission angle may be variable. In this case, high-accuracy scanning of the convergence position is possible, for example, by controlling the driving of the XY scan units 25 and 55.

In First to Fourth Embodiments, the numerical aperture NA of the pulsed laser beam emerging from the objective lens 35 is maintained, regardless of the Z scan. However, the numerical aperture NA may vary according to the Z scan. It is also possible to vary the numerical aperture NA by driving, for example, the beam expender 13 according to various parameters (for example, the convergence position of the pulsed laser beam in Z direction).

In addition to the configurations of the embodiments above, a configuration may be provided that corrects the aberration caused by scanning of the pulsed laser beam. For example, an aberration may be corrected with a device provided upstream of the XY scan units 25 and 55 to bring about changes in the wave front of the pulsed laser beam. It is not required to separately provide the deflecting device for scanning the pulsed laser beam in X direction, and the deflecting device for scanning the pulsed laser beam in Y direction. Specifically, the ophthalmic laser surgical apparatus may use a single deflecting device for the XY scanning of the pulsed laser beam.

In Third and Fourth Embodiments, the reflecting units 71 and 81 with two reflectors change the direction of travel of the pulsed laser beam 180°. The convergence position is scanned in Z direction as a result of the movement of the reflecting units 71 and 81. However, the reflecting units 71 and 81 may have different configurations. For example, it is not necessarily required to provide two reflectors for the reflecting units 71 and 81. The reflecting units 71 and 81 may be realized by using a prism, for example.

What is claimed is:

1. An ophthalmic laser surgical apparatus for converging a pulsed laser beam in a tissue of a patient's eye for the treatment of the eye, the apparatus comprising:
   a laser light source configured to emit the pulse laser;
   an XY scan unit which includes at least one deflecting device configured to deflect the pulsed laser beam emitted by the laser light source, and which is configured to scan the pulsed laser beam in a direction crossing an optical axis of the pulsed laser beam by the deflecting device;
   a light guiding optical element provided downstream of the deflecting device of the XY scan unit on the optical path of the pulsed laser beam, the light guiding optical element having refractive power and guiding the pulsed laser beam toward the downstream side of the optical path;
   an objective lens that causes the pulsed laser beam, which passes through the XY scan unit and the light guiding optical element, to converge in the tissue;
   a Z scan unit configured to scan a convergence position of the pulsed laser beam in a Z direction along the optical axis by varying the optical path length between the light guiding optical element and the objective lens while the objective lens is fixed in position on the optical path; and
   a relay unit that includes an upstream relay optical element positioned downstream of the XY scan unit, and a downstream relay optical element positioned between the upstream relay optical element and the objective lens; and
   wherein the Z scan unit varies an optical path length between the upstream relay optical element and the objective lens by moving along the optical axis an optical unit that includes the XY scan unit and the upstream relay optical element serving as the light guiding optical element; and
   the upstream relay optical element is disposed at a position where a primary focal point of the upstream relay optical element is on the pivot point of the deflecting device.

2. The ophthalmic laser surgical apparatus according to claim 1, wherein
   a position of an optical element disposed downstream of the Z scan unit on the optical path remain constant on the optical path regardless of the driving of the Z scan unit, and
   a primary focal point of the light guiding optical element is on a pivot point where principal rays of all the pulsed laser beams scanned by the deflecting device on the upstream side of the light guiding optical element pass through.

3. The ophthalmic laser surgical apparatus according to claim 2, wherein a principal rays of all the pulsed laser beams scanned by the XY scan unit pass through the primary focal point of the objective lens.

4. The ophthalmic laser surgical apparatus according to claim 1, wherein a distance between a principal plane of a refractive optical element which has refractive power and is closest to the objective lens from among optical elements positioned upstream of the objective lens on the optical path and a principal plane of the objective lens is equal to a sum of a focal length of the refractive optical element and a focal length of the objective lens.

5. The ophthalmic laser surgical apparatus according to claim 1, wherein the XY scan unit includes:
   an X deflecting device configured to deflect the pulsed laser beam in an X direction crossing the optical axis;
   a Y deflecting device configured to deflect the pulsed laser beam, which is scanned by the X deflecting device, in a Y direction crossing the optical axis and the X direction; and
   an XY relay unit disposed on the optical path between the X deflecting device and the Y deflecting device, and that relays the X deflecting device to the Y deflecting device with an upstream XY relay optical element, and a downstream XY relay optical element positioned downstream of the upstream XY relay optical element,
   wherein the Z scan unit varies the optical path length between the upstream relay optical element and the objective lens by moving along the optical axis an optical unit that includes the X deflecting device and the upstream XY relay optical element serving as the light guiding optical element.

6. The ophthalmic laser surgical apparatus according to claim 1, wherein the Z scan unit includes:

a reflecting unit disposed on the optical path and configured to reflect the pulsed laser beam; and a Z scan driving section configured to vary the optical path length by moving the reflecting unit.

7. The ophthalmic laser surgical apparatus according to claim 6, further comprising:

a relay unit that includes an upstream relay optical element positioned downstream of the XY scan unit, and a downstream relay optical element positioned between the upstream relay optical element and the objective lens, wherein the reflecting unit is provided on the optical path between the upstream relay optical element and the downstream relay optical element.

8. The ophthalmic laser surgical apparatus according to claim 6, wherein the XY scan unit includes:

an X deflecting device configured to deflect the pulsed laser beam in an X direction crossing the optical axis;

a Y deflecting device that deflects the pulsed laser beam, which is scanned by the X deflecting device, in a Y direction crossing the optical axis and the X direction; and an XY relay unit disposed on the optical path between the X deflecting device and the Y deflecting device, and that relays the X deflecting device to the Y deflecting device with an upstream XY relay optical element, and a downstream XY relay optical element positioned downstream of the upstream XY relay optical element, wherein the reflecting unit is provided on the optical path between the upstream XY relay optical element and the downstream XY relay optical element.

9. The ophthalmic laser surgical apparatus according to claim 1, further comprising a Z scan unit disposed between the laser light source and the XY scan unit on the optical path, the Z scan unit being configured to scan the convergence position of the pulsed laser beam in the Z direction.

10. The ophthalmic laser surgical apparatus according to claim 1 further comprising a beam diameter varying section disposed between the laser light source and the XY scan unit on the optical path, the beam diameter varying section being configured to vary a beam diameter of the pulsed laser beam.

11. An ophthalmic laser surgical apparatus for converging a pulsed laser beam in a tissue of a patient's eye for the treatment of the eye, the apparatus comprising:

a laser light source configured to emit the pulse laser;

an XY scan unit which includes at least one deflecting device configured to deflect the pulsed laser beam emitted by the laser light source, and which is configured to scan the pulsed laser beam in a direction crossing an optical axis of the pulsed laser beam by the deflecting device;

a light guiding optical element provided downstream of the deflecting device of the XY scan unit on the optical path of the pulsed laser beam, the light guiding optical element having refractive power and guiding the pulsed laser beam toward the downstream side of the optical path;

an objective lens that causes the pulsed laser beam, which passes through the XY scan unit and the light guiding optical element, to converge in the tissue;

a Z scan unit configured to scan a convergence position of the pulsed laser beam in a Z direction along the optical axis by varying the optical path length between the light guiding optical element and the objective lens while the objective lens is fixed in position on the optical path; and a relay unit that includes an upstream relay optical element positioned downstream of the XY scan unit, and a downstream relay optical element positioned between the upstream relay optical element and the objective lens; and wherein a reflecting unit for reflecting a pulsed laser is disposed on the optical path between the upstream relay optical element and the downstream relay optical element, and the reflecting unit is moved to vary the optical length between the upstream relay optical element and the downstream relay optical element while the position of the upstream relay optical element and the position the downstream relay optical element is fixed; and the upstream relay optical element is disposed at a position where a primary focal point of the upstream relay optical element is on the pivot point of the deflecting device.

* * * * *